(12) United States Patent
Nastro (10) Patent No.: US 7,900,636 B1
(45) Date of Patent: Mar. 8, 2011

(54) FINGER SUCKING DETERRENT DEVISE AND METHOD OF USE OF SAME

(76) Inventor: April Nastro, Mongaup Valley, NY (US)

( * ) Notice: Subject to any disclaimer, the term of this patent is extended or adjusted under 35 U.S.C. 154(b) by 81 days.

(21) Appl. No.: 11/796,688

(22) Filed: Apr. 27, 2007

(51) Int. Cl.
*A61F 5/37* (2006.01)
*A41D 19/01* (2006.01)
(52) U.S. Cl. ............... 128/880; 128/881; 2/158
(58) Field of Classification Search .......... 128/880, 128/881; 2/158, 159, 160
See application file for complete search history.

(56) References Cited

U.S. PATENT DOCUMENTS

| | | | |
|---|---|---|---|
| 1,345,783 A | 7/1920 | Kelly | |
| 1,794,515 A | 3/1931 | Davis | |
| 1,929,318 A | 10/1933 | Klosky | 128/133 |
| 2,143,927 A | 1/1939 | Thompson | 128/133 |
| 2,442,176 A | 5/1948 | Orr et al. | 128/133 |
| 2,498,122 A * | 2/1950 | Haniuk | 128/879 |
| 2,633,126 A | 3/1953 | Newmark | 128/133 |
| 4,103,362 A * | 8/1978 | Blakeman | 2/161.1 |
| D351,930 S * | 10/1994 | Snider et al. | D29/113 |
| 5,797,405 A | 8/1998 | Brock | 128/878 |
| 5,799,333 A * | 9/1998 | McGarry et al. | 2/161.6 |
| 6,009,557 A * | 1/2000 | Witta | 2/159 |
| 6,044,493 A * | 4/2000 | Post | 2/167 |
| 6,155,084 A * | 12/2000 | Andrews et al. | 66/174 |
| D516,753 S * | 3/2006 | Grissom | D29/113 |

FOREIGN PATENT DOCUMENTS

GB 2089196 A * 6/1982

OTHER PUBLICATIONS http://www.stopthumbsucking.net/.*
Catalogue "Leaps and Bounds" Spring Preview 2006 p. 27.
Catalogue "Leaps and Bounds" Spring Preview 2007 p. 23.

* cited by examiner

*Primary Examiner* — Patricia M Bianco
*Assistant Examiner* — Ophelia Hawthorne
(74) *Attorney, Agent, or Firm* — Sandra M. Kotin (57) ABSTRACT

A device to deter finger sucking is a partial cover for the hand with at least one finger stall encompassing the finger or fingers usually sucked. The device can also have individual finger stalls, each accommodating one finger. The device has a ribbed cuff that is elastic so the child can put the device on and take it off himself. The device is made of a knitted fabric that is stretchable throughout. This characteristic makes it possible for the child to remove his finger or fingers from the one or more finger stalls and move the device upward on his arm and out of the way when eating, washing, for personal hygiene and certain school activities and thereafter quickly replace it on the hand with the finger or fingers in the one or more finger stalls. The child has complete control over its use. This device should be maintained on the hand or arm at all times except when bathing. The device can be colorful and decorated in a manner that is attractive to the child. The knitted fabric provides a dry unpleasant mouth feel and allows air to pass through the fibers so that no suction is attained during sucking. Without suction there is no satisfaction and the child is deterred from sucking his finger or fingers until he stops altogether.

2 Claims, 4 Drawing Sheets

FINGER SUCKING DETERRENT DEVISE AND METHOD OF USE OF SAME

FIELD OF THE INVENTION

The instant invention relates to a device and method for deterring the habit of finger-sucking by a child

BACKGROUND OF THE INVENTION

Many infants suck their thumbs or other fingers, a habit which is usually outgrown by the time a child is walking and talking. However, a small percentage of children retain that habit even continuing into their early school years. Finger sucking can result in a variety of dental problems which may become serious malformations of the deciduous teeth and when the activity is continuous and extends beyond the sixth year there will be problems when the permanent teeth erupt. With older children the habit may lead to teasing by their peers and sometimes being singled out and embarrassed by an inconsiderate teacher.

Over the years a variety of devices have been developed to break an infant or child of the habit of sucking his thumb. The sucking of another finger or fingers has not been so specifically addressed. Early patents for devices to deter thumb sucking appear more like torture contrivances then useful devices. In U.S. Pat. No. 1,345,783, Kelly taught a device that consisted of an adjustable bracelet that is locked around the wrist of an infant. A bar is screwed into the bracelet and extends upward. Attached to the bar is a thumb ring that surrounds the thumb and holds it in one orientation. A piece of the bar is bent over at the top to prevent the infant from obtaining suction when he tries to suck his thumb. The bracelet and height of the thumb ring are adjustable to accommodate different size hands and the infant's growth.

Other devices to deter thumb sucking consist of rigid tubes that fit over the thumb and are affixed to the wrist with a tie or band. Such devices were taught by Davis in U.S. Pat. No. 1,794,515 and Klosky in U.S. Pat. No. 1,929,318. These devices restrict any movement of the thumb and prevents the wearer from grasping and holding any object. Thompson devised a version that fits over the thumb and is tied around the wrist, but his device was made of a coiled flexible wire so it was somewhat flexible and the child could have some thumb movement though grasping or retaining any object appears impossible. (U.S. Pat. No. 2,143,927)

Newmark in U.S. Pat. No. 2,633,126 taught the use of a cylindrical cap that fits over the thumb and had a tongue extending downward to the wrist. There were openings at the lower part of the tongue through which a string was threaded and tied around the wrist to retain the device. This cap had ribs along the inner surface that cooperated with openings to allow air to flow in and prevent the formation of suction when the child sucked her thumb. The device was made of rubber or a resilient plastic so the child could have some grasping ability while wearing the device. However, a child could bite through a rubber cap and also easily remove the device from her hand.

Orr et al., in U.S. Pat. No. 2,442,176, disclosed a plastic cylinder that was closed at one end and open at the other to receive the thumb. A woven sheath was attached to the inside of the cylinder at the closed end. The thumb was inserted into the sheath and any attempt to remove it only tightened the hold. A U-shaped key could be used to widen the sheath so the user could remove his thumb. An ornamental figure could be attached to, the cylinder. This device would also make it impossible for the wearer to grasp or retain any object in the hand.

In U.S. Pat. No. 5,797,405, Brock devised a glove made of terry cloth with the pile on the outside and having only a finger sheath for the thumb. The remaining fingers were uncovered. The glove had a slit wrist band which could be closed using a snap to maintain the glove on the hand. The distal end of the thumb sheath was coated with latex in such a manner that many terry cloth pile loops formed protrusions coated with the latex to provide an unpleasant sensation in the mouth. The latex coating could easily become detached in pieces when a child sucked or chewed on the thumb cover posing a choking problem. Latex can also become a serious a problem if the child was allergic to it. Additionally, the dexterity of the user would be limited by the clumsy thumb cover.

Though some of the prior art devices may be used for infants, a child of three or older can remove many of them. The rigid thumb covers prevent a child from grasping an object and are not only uncomfortable and unsightly, but can interfere with proper hand coordination and development. Plastic and latex devices can be bitten off and, as noted above, pose very serious choking problems.

A more recent device to discourage thumb sucking has been advertised in the Leaps and Bounds catalogue for Spring 2006 at page 27. The device is made of clear plastic and is affixed to the wrist with a flexible bracelet or band. The device is a rigid tube, wider at the bottom, that encloses the entire length of the thumb and has two protrusions that extend to the wrist through which the band is threaded. When the child goes to suck his thumb it is the plastic tube that goes into the mouth. The Leaps and Bounds catalogue for Spring 2007 at page 23 also advertises individual finger guards for the remaining four fingers. One or more can be worn at a time. These finger guards are also affixed to the wrist with a flexible band or bracelet through an extension of the finger guard. These clumsy devices prevent any flexing or other movement of the thumb or encased fingers. A child wearing this device is prevented from grasping an object in his hand. The devices are advertised in three sizes to accommodate children from 3-4 years, 5-6 years and the large size, 7-15 years. It appears that a child of 5 or older could easily remove this device from his hand and a child attending school or even being seen by a peer would not want to wear this device at all.

None of the prior art finger sucking deterrents can be worn on both hands at the same time since to do so would render the child unable to anything with his hands. They all prevent free movement and grasping activity of the hand and any flexing of the finger being covered.

There is a need for a device to discourage thumb and finger sucking habits in young children. There is need for such a device that can be controlled by the child so he will wear it; one that poses no choking danger; one that does not interfere with the dexterity and development of the hand and one that can be removed and held safely and conveniently on the arm when the child engages in activities that necessitate its removal. There is a need for such a device that the child will not be embarrassed to wear and so will continue to use the device as long as needed. There is a need for a device that can be worn 24 hours a day and not hinder any of the child's activities and is comfortable during sleep. There is a need for a finger sucking deterrent device that can be worn on both hands at the same time if the need is present.

BRIEF SUMMARY OF THE INVENTION

The present invention provides a device to be worn by a child from three years of age and older. The device is soft, flexible and not unsightly. It is essentially a partial hand cover made of a knitted fabric. The fabric is not tightly knitted so that air can be pulled between the fibers when the child sucks his finger or fingers. The device has a flexible and resilient wrist band and finger stalls that cover only the one or two fingers on which the child habitually sucks. The knitted fabric has a fuzzy or dry mouth feel and does not produce suction when the child sucks on his finger or fingers while wearing the device.

It is an object of the present invention to provide a device to deter finger sucking by a young child, or person of any age.

It is another object of the present invention to provide a device that the child will wear and over which the child has complete control.

Another object of the present invention is to provide a device that can be removed from the hand during certain activities but is maintained on the arm so it does not get lost or soiled.

A still further object of the present invention is to provide a device that will not restrict or prevent any degree of movement or the grasping capabilities of the child's hand, wrist or fingers.

It is another object of the present invention to provide a device that will have an unpleasant mouth feel and prevent the formation of suction when the child sucks on his finger or fingers while wearing the device.

A further object of the present invention is to provide a device that can comfortably be worn at night so that it is on the hand if the child unconsciously sucks his finger or fingers during sleep.

A still further object of the present invention is to provide a device that is completely safe to use as well as being washable, comfortable, and attractive to wear.

It is another object of the present invention to provide a device the can be worn 24 hours a day regardless of the activities in which the child is engaged.

An object of the present invention is also to provide a device that can be worn on both hands at the same time and not limit any of the activities of the user.

The instant invention is a method of deterring a child's habit of finger sucking which comprises the steps of obtaining at least two finger sucking deterrent devices made of a knitted fabric, each comprising: a resilient cuff configured to be placed on the wrist and easily removed therefrom and also to be moved upward on the arm and retained thereon, at least one stretchable tubular finger stall with a closed upper end and a lower end, said at least one finger stall being sized to accommodate at least one finger and adapted to enable the child to remove the at least one finger from the at least one finger stall while retaining the device on the hand and to move the device upward on the arm and thereafter move the device downward on the arm and replace the at least one finger in the at least one finger stall, said at least one finger stall being composed of a fabric that permits air to pass through it, and a stretchable body for joining the at least one finger stall to the cuff, said body having at least one opening of sufficient size for the device to be put on and taken off with ease and so that the child can remove the at least one finger from the at least one finger stall and replace the at least on finger into the at least one finger stall while retaining the device on the hand; placing one of the at least two finger sucking deterrent devices on his or her hand such that the at least one finger being sucked is disposed within the at least one finger stall; and removing the at least one finger from the at least one finger stall and pushing the device upward on his or her arm during eating and washing. The invention further comprises the steps of moving the device downward on the arm and replacing the at least one finger into the at least one finger stall after eating and washing, sucking on the at least one finger through the at least one finger stall and having air pulled through the fabric so that he or she gets a dry and unpleasant mouth feel and obtains no satisfaction in the sucking, removing the at least one finger from the at least one finger stall and moving the device upward on the arm during a school activity, moving the device downward on the arm and replacing the at least one finger into the at least one finger stall after completion of the school activity, replacing the device with another of the at least two devices when the one device becomes soiled, removing the device from his or her hand when bathing and replacing the device on his or her hand thereafter, and wearing one of the at least two devices twenty four hours a day until he or she no longer sucks his or her at least one finger. As the child repeatedly sucks his or her at least one finger through the at least one finger stall no suction is attained, there is a dry and unpleasant mouth feel and gradually the child loses interest in sucking the at least one finger and can cease wearing the device altogether. The instant invention is also a device made of a stretchable knitted fabric to discourage a child's habit of finger sucking. The device comprises a tubular finger stall configured to accommodate the finger being sucked, the finger stall having a closed upper end and a lower end such that when the child sucks the finger contained in the closed upper end of the finger stall air is drawn through the knitted fabric and no suction is attained, a ribbed cuff configured to be placed on the child's wrist, to be pushed upward on the arm and retained thereon while the child participates in an activity and to be returned to the wrist at the conclusion of the activity, and to be removed from the wrist for washing. There is a body for joining the lower end of the finger stall to the cuff, the body being sufficiently stretchable to enable the child to remove the finger from the finger stall, push the cuff upward on the arm, return the cuff to the wrist and replace the finger in the finger stall without removing the device from the hand. The device is made of a fiber that is washable, non-pilling and sufficiently strong to withstand sucking and biting by the child. When the child wears the device and sucks his or her finger contained in the finger stall the child gels no satisfaction from the sucking and becomes discouraged from doing so.

The invention is also a device to be worn on a hand to deter finger sucking by a child. The device comprises a resilient cuff for reversible application to a wrist, secure retention on the wrist, and adapted to be pushed upward on an arm and retained thereon during the participation in an activity and thereafter moved downward and replaced on the wrist. There is at least one stretchable tubular finger stall closed at one end, the at least one finger stall being sized to accommodate at least one finger and being sufficiently stretchable to enable the wearer to remove the at least one finger from the at least one finger stall while retaining the device on the hand, moving the device upward on the arm during participation in the activity and thereafter moving the device downward on the arm, and replacing the at least one finger in the at least one finger stall. The at least one finger stall is composed of a fabric that permits sufficient air to pass through it to prevent suction from being established when the child sucks on the at least one finger within the at least one finger stall while allowing the child to pick up, grasp and hold objects. There is a stretchable body for joining the at least one finger stall to the resilient cuff, the body having at least one opening of sufficient size to expose the remaining fingers. The device is sufficiently close fitting and comfortable that it can be worn day and night, will not interfere with sleep and will not become dislodged when worn during sleep. When the child wears the device and sucks on the at least one finger enclosed in the at least one finger stall, air is drawn through the fabric, no suction is attained and there is a dry and unpleasant mouth feel so the child gets no satisfaction from the sucking and becomes deterred from doing so.

Other features and advantages of the invention will be seen from the following description and drawings.

DETAILED DESCRIPTION OF THE INVENTION

Many children continue to suck their thumbs or other fingers long after their toddler years have passed. The longer a child continues in this habit, the more difficult it is to break. As the child gets older, he can remove most, if not all, of the devices designed to break this habit. It therefore becomes necessary to use a device that the child can control in the hope that this will encourage the child to use it. If the chosen device looks "cool" to his contemporaries, feels comfortable and does not restrict any movement or activities, it is more likely that the child will use it, or even show it off to his friends.

Figure 1:
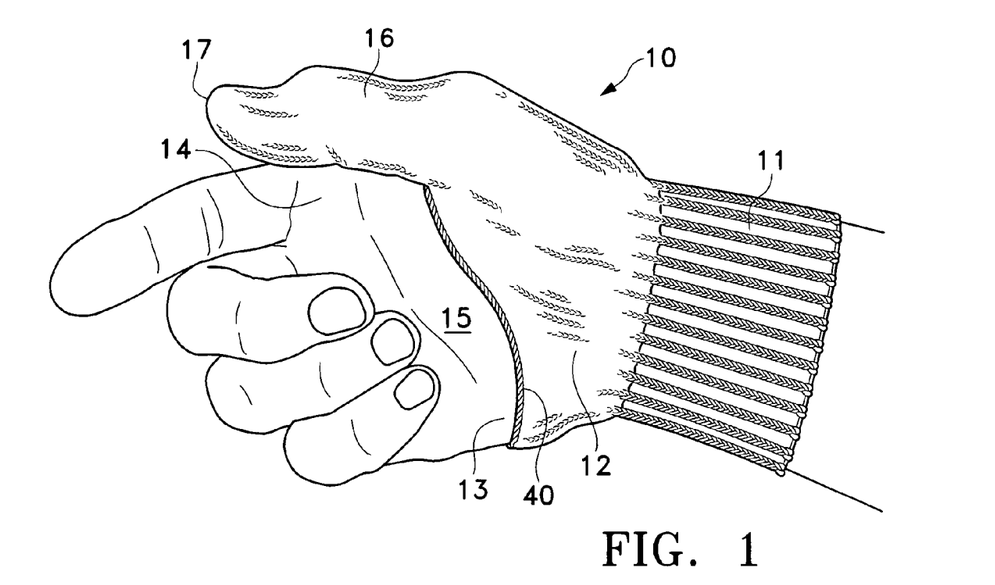
FIG. 1 is a palm view of a device of the present invention prepared for a thumb sucker and applied to a user's hand.

FIG. 1 may show a first embodiment 10 of the invention designed to deter thumb sucking. This device may be a partial hand cover that has a resilient (capable of recovering size and shape after deformation) cuff 11 to fit snugly against the wrist, but may be capable of expanding sufficiently to permit the device to be easily put on and taken off. Adjacent to the cuff and integral therewith may be the body 12 of the device. The body 12 may also be capable of stretching without losing its original shape, yet not necessarily to the extent of the cuff 11, and may fit over most of the lower portion of the hand 13 extending substantially from the wrist (the top of the cuff 11) to the base of the knuckles. The upper part of the hand 14 closest to the knuckles may be exposed and unencumbered. A portion of the palm 15 may also be exposed. Integral with and of the same composition as the body 12 and extending therefrom may be a thumb stall 16. The thumb stall 16 may completely cover the thumb and may be tubular and closed at the top 17. Again, the fabric of the thumb stall 16 may cling to the thumb with no slack, but not so tight as to be uncomfortable. This device 10 may be worn at all times, night and day, except when bathing. The thumb may be removed from the thumb stall but the device may be moved upward and retained on the arm when the child eats, washes, for hygienic purposes, and during some school activities.

It may be especially important that the device be worn at night. Often a child will suck his thumb during sleep and be totally unaware that he is doing so. The resilient nature of the fabric of which the device is composed may cause it to be snug enough, yet comfortable, so that the device may be worn during sleep. The device may not be dislodged during sleep, even when worn by a restless child.

Figure 2:
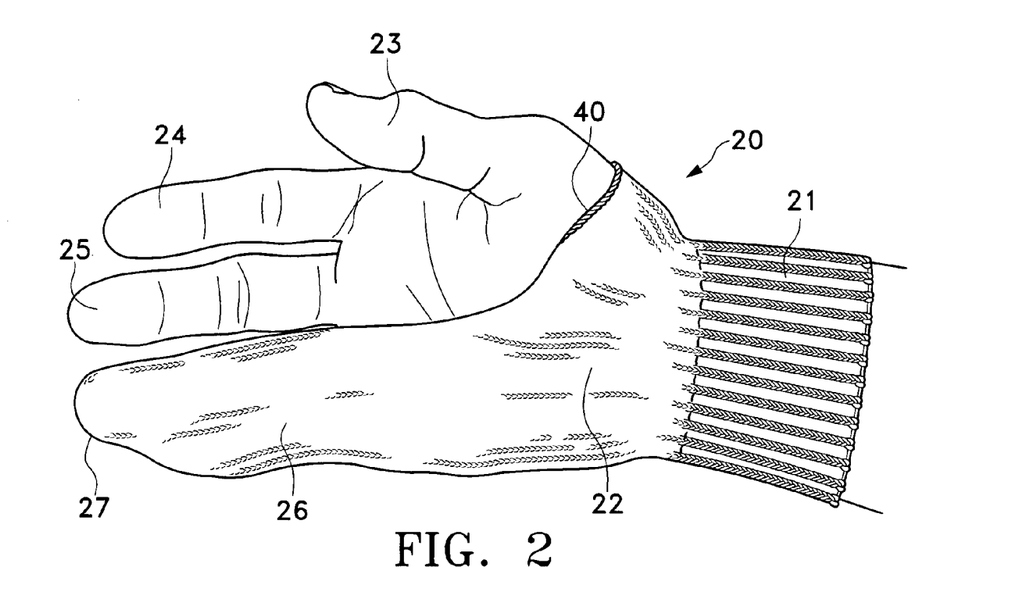
FIG. 2 is a palm view of a device of the present invention prepared for a child that sucks the fourth and fifth fingers and applied to a user's hand.

The second embodiment 20, seen in FIG. 2, may also have a snug resilient cuff 21, a body 22, and a tubular finger stall 26 that may be stretchable and closed at the outer end 27. The second embodiment 20 may be designed for the child that sucks two adjacent fingers, other than the thumb. Thus the finger stall 26 of the second embodiment may be integral with the body 22 and large enough to encompass both of the fingers together, snuggly yet comfortably. When the second embodiment 20 is worn, the thumb 23, and other fingers 24 and 25 may be completely exposed and unencumbered.

The third embodiment 30 seen in FIGS. 3, 4, 5 and 6 may also be designed for the child that sucks two adjacent fingers. There may be a cuff 31, a body 32 and two tubular finger stalls 33 and 34 with closed outer ends 35 and 36. These finger stalls 33 and 34 may be oriented and sized to comfortably enclose two adjacent fingers while permitting full movement and grasping by those fingers in any type of activity. This embodiment may accommodate any two adjacent fingers except the thumb. There may be a wide opening 37 along each side of the device (see FIG. 5) for ease of putting on and removal. These wide openings 37 also allow for some air circulation so the hand does not become too warm.

The third embodiment 30 exhibiting two adjacent finger stalls permits maximum dexterity and allows each finger to function in the same manner as when not enclosed in a knitted finger stall.

Figure 3:
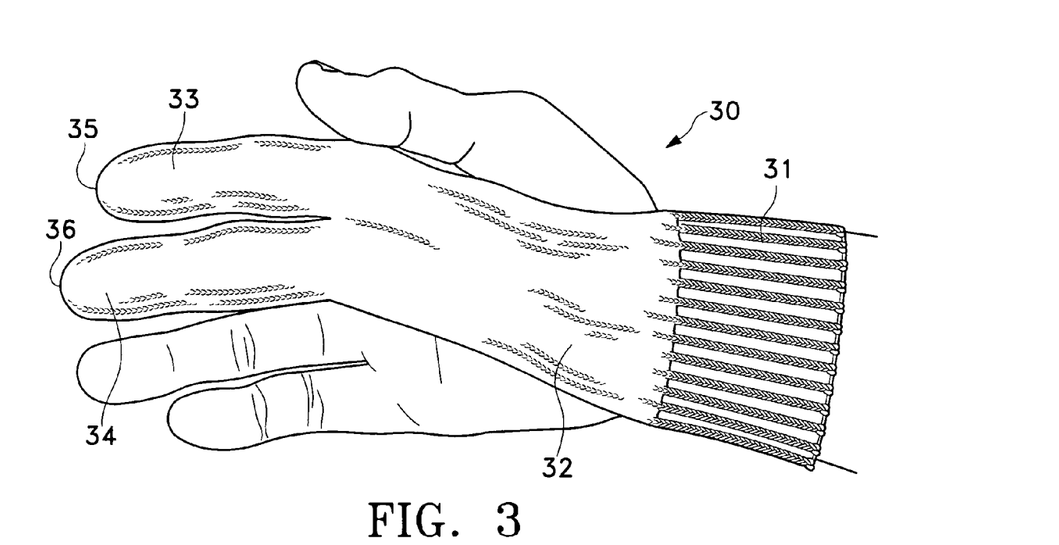
FIG. 3 is a palm view of another embodiment of the device of the present invention applied to the hand of a child that sucks the second and third fingers.
Figure 4:
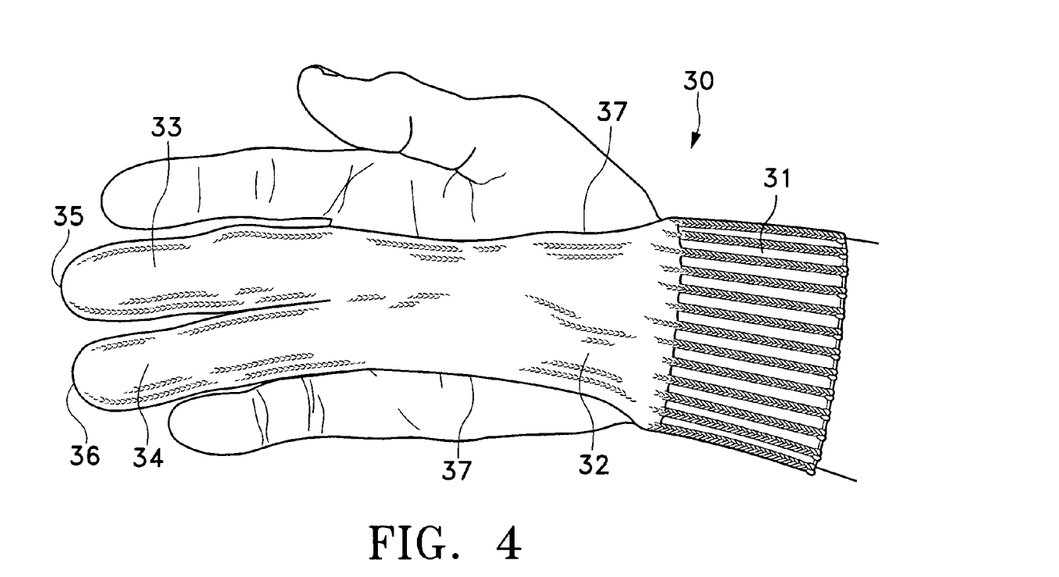
FIG. 4 is a palm view of a the embodiment of FIG. 3 applied to the hand of a child that sucks the third and fourth fingers.
Figures 5, 6:
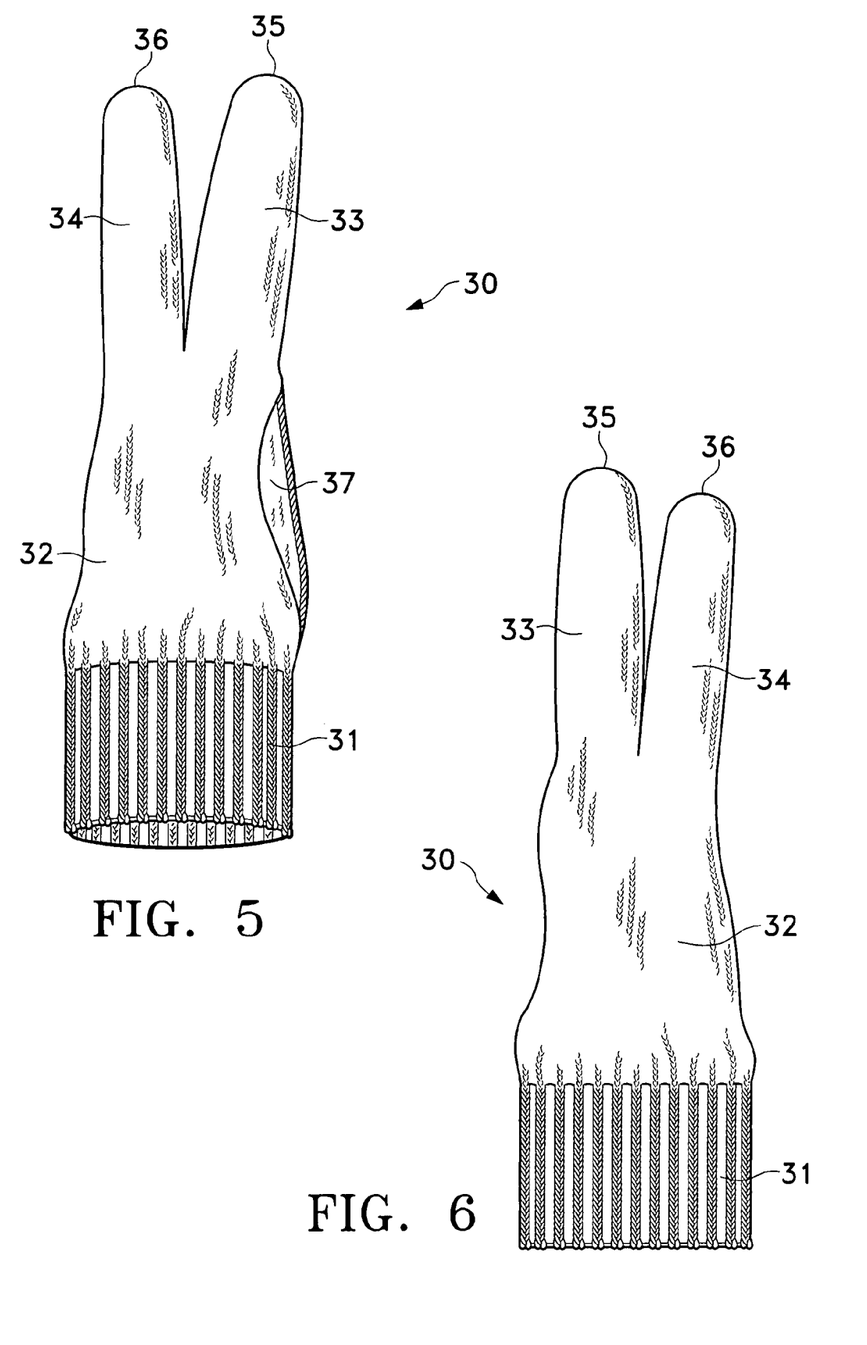
FIG. 5 is a back perspective view of the device FIG. 3.
FIG. 6 is a front plan view of the device of FIG. 3.

It may be possible to have a single design serve any child that sucks two adjacent fingers. However, the body of the device of the third embodiment 30 may have somewhat more slack on one side than on the other. This may permit the front and back to be reversed depending upon the particular two fingers involved and so that the best fit and maximum comfort may be attained.

Usually when a child sucks more than one finger, those fingers are adjacent to each other. However, for a child that sucks only one finger, other than the thumb, two non-adjacent fingers, or the thumb and any other finger or fingers, suitable designs and modifications may be made for a suitable device that follows the teachings of the present invention. The device of the present invention may also be made to be worn on a right hand or a left hand. Devices of the present invention may also be worn on both hands at the same time, if necessary.

All of the embodiments of the present invention may be made of a soft, elastic, i.e., stretchy, fabric that conforms to the shape of the wrist, the covered portion of the hand and the finger or fingers which must be enclosed. This fabric may be made of any resilient fiber that is washable and holds its shape against distortion after repeated washings. It may be preferable that the fabric be knitted. The entire device may be knitted in a single unit with a ribbed cuff that stretches over the hand for easy on and off. The knitted fabric may fit loosely enough to accomplish the easy on and off and may be tight enough to cling closely to the hand and fingers with no gaps or slack. It may not be so tight as to cut off circulation or cause discomfort. The fiber of which the device is knitted may be natural or synthetic, but may not pill, discard fibers or tear easily. It may have an unappealing mouth feel and not permit suction to form without being overly objectionable to the child. The fiber used for the device may be strong enough to withstand repeated biting and chewing without coming apart.

The knitted fabric may exhibit sufficient spacing between the fibers such that when a child attempts to suck the encased finger or fingers air may be pulled through the fabric so that no suction can be established. Without suction the child may not get the usual satisfaction from the sucking action and soon may begin to tire of sucking his finger or fingers altogether.

Depending upon the fiber chosen to construct the device, additional latex fibers or fibers such as LYCRA®, spandex® or other such elastic fiber may be added to achieve the desired degree of resiliency. More of the extra fiber may be added to the ribbed cuff then to the body or finger stall. In addition to the cuff there may be a narrow band of ribbing or elastic fiber reinforcement to increase the resiliency along the upper edge of the body 12 and 22 and along the free edge of the finger stall in the first and second embodiments 10 and 20 as may be seen in FIGS. 1 and 2. The reinforced band may also be present along the side edges 37 in the third embodiment 30. This band may prevent gapping of the fabric along these edges and permit the fabric to better cling to the hand.

This device may not be suitable for an infant but may be geared to a young child, preferably from the age of three. It may be used by a child of any age who can comprehend how to use it. It may also be used by a teenager or adult. The device may easily be put on and taken off by a child. The elastic wrist band may enable the putting on and taking off to be accomplished easily and may ensure complete control to the child. When the child takes responsibility for wearing the device, and has complete control over it, there may be a greater chance that it will be worn and that the goal of stopping finger sucking will be achieved. With many celebrities wearing finger-less, partial-finger and other fancy hand covers, children seeing their friends wearing this device may find it "cool" and offer compliments, thus giving encouragement to the wearer to want to wear it.

The fabric of the device may be made in any color, colors or pattern desired. The more decorative or interesting to the child the more likely it may be to be worn. The device may also sport patches with favorite cartoon, book or movie characters that the wearer can show off to friends.

When the device is used, it may be worn twenty four hours a day except when the child bathes. For eating, hygiene and certain school activities it may be retained on the arm. For this reason, once the use is begun, the child may have at least two and preferably three or four of the devices at his disposal. This may enable time for laundering and replacements if one becomes damaged. The child may require constant use of the device to achieve success in breaking the finger-sucking habit. Typically, the device may be worn from one to three months. Since each child is different, the time may vary and longer or shorter periods may be needed.

Features of this device that may make it very practical, easy to use by the child, and favored by the parents may be first, that it does not restrict hand movement for grasping, dexterity and normal hand development and, second the ability to remove the finger or fingers from the finger stall without removing the device from the arm. The resilient nature of the wrist band as well the other parts of the device may make this possible. Once the finger(s) are removed from the finger stall(s), the device may be pushed up the arm out of the way yet retained on the arm. This way the device is not entirely removed from the arm and put aside where it can be misplaced or forgotten. The ability to remove the finger(s) and maintain the device on the arm may also make it possible for the child in school to free his finger(s) when necessary according to the activity in which he is engaged and replace the device on his finger(s) as soon as the activity is concluded. All the while the device remains on his person, in his control, and cannot be misplaced. Parents do not have to be concerned that the device may be lost. Even a three year old child can accomplish this with ease.

Figure 7:
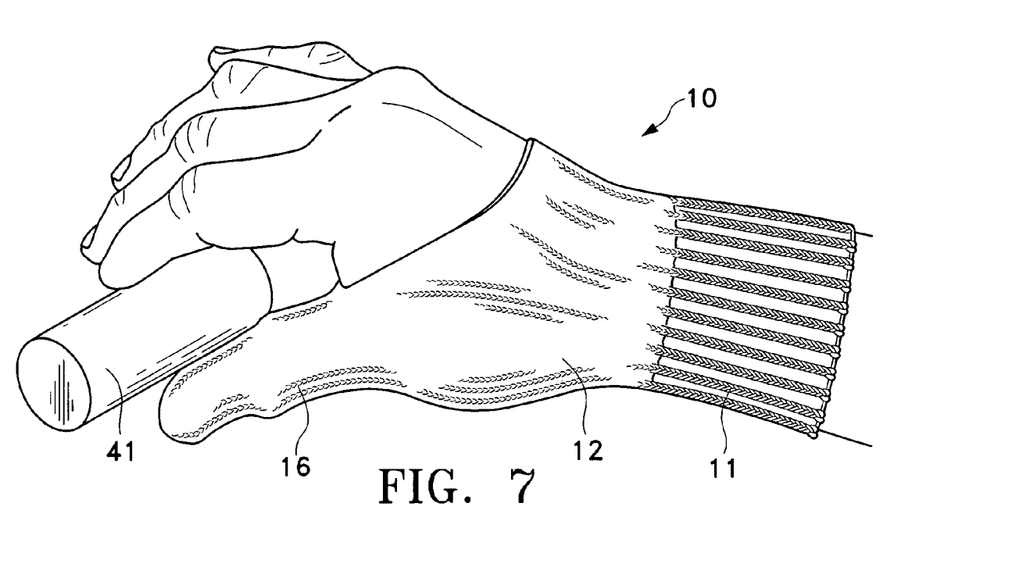
FIG. 7 is a perspective view of a device of the present invention prepared for a thumb sucker and applied to the hand of a user who is holding an object.
Figure 8:
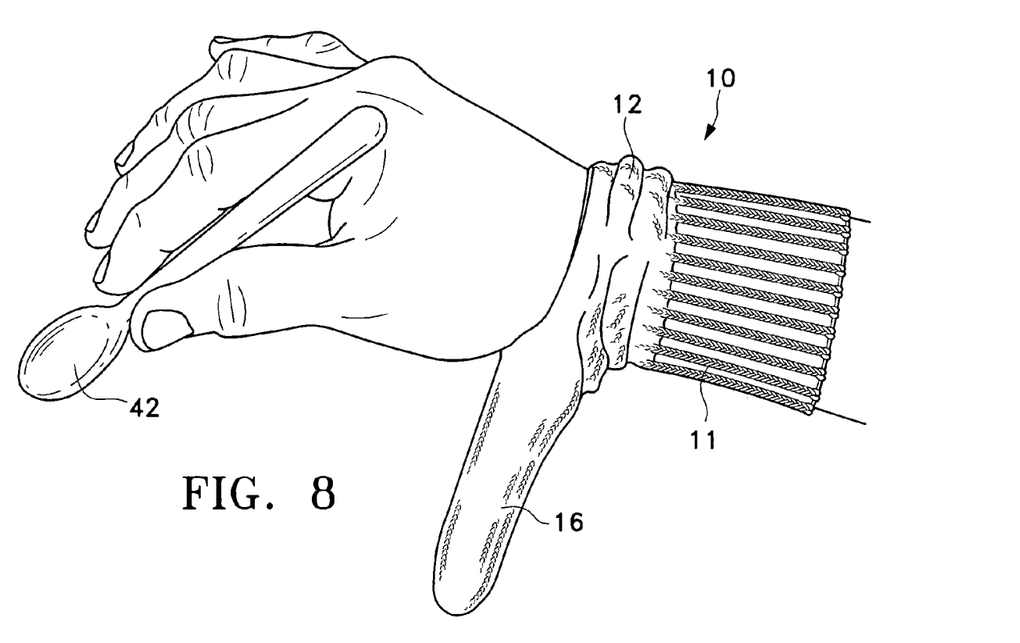
FIG. 8 is a perspective view of a device of the present invention rolled up on the arm of a user during eating.

Since the device is not bulky it may not restrict activities such as eating, grasping and holding objects, writing, drawing and even playing some musical instruments. FIG. 7 shows how an object 41 may easily be grasped while wearing the first embodiment 10 of this invention. FIG. 8 shows a hand holding a spoon 42 with the finger(s) removed from the finger stall(s) and the device pushed up the arm and out of the way.

Wearing the device of the instant invention and attempting to suck on a finger or fingers may result in a failure to obtain the suction that creates the satisfaction found in finger sucking. This occurs because air may be drawn through the openings between the fibers in the knitted fabric preventing suction from forming. Suction is created when air is not drawn into the mouth. One of the reasons this device may be so successful is the dry feeling in the mouth when the covered finger(s) is/are sucked on. This feeling may be objectionable but not harmful in any way. By removing the possibility that suction is established and which provides the satisfaction to the child, the urge to suck the finger(s) is diminished until it is no longer viable.

When eating, the enclosed finger(s) may be removed from the finger stall(s) and the device moved up the arm out of the way. The child may finish eating and wash her hands and then move the device down the arm and replace the finger(s) in the finger stall(s). This removal and replacement without actually taking the device off the hand may be repeated throughout the day as necessary and may become automatic to the child. Since the finger(s) is/are only removed from the finger stall(s) when the child engages in a particular activity or task and is/are thereafter quickly replaced into the finger stall(s), the finger(s) may otherwise always be covered, as when the child is not specifically engaged, that is, the times when finger sucking is most likely to occur.

The time frame during which the device may be worn may differ from child to child and also according to the age of the child and the amount of time spent in the activity of finger sucking. Most devices developed to discourage this activity are unsightly and uncomfortable as well a being an embarrassment to the child.

This device is not unsightly, is comfortable to wear, and gives complete control to the child. This device may not cause embarrassment and, in fact, may be envied by friends. The device of the present invention may therefore achieve its goal quickly. A child can wear a device on each hand, if necessary, and still participate in any and all activities. The devices can be moved up the arms and held out of the way when the activity dictates and the child has complete control over them, even when worn on both hands.

While several embodiments of the instant invention have been illustrated and described in detail, it is to be understood that this invention is not limited thereto and may be otherwise practiced within the scope of the following claims.

This parts list is for examination purposes only and should not be published with the patent.

NASTRO PARTS LIST 10 first embodiment
11 cuff
12 body
13 lower part of hand
14 upper part of hand
15 palm
16 thumb stall
17 closed end of thumb stall
18
19

20 second embodiment
21 cuff
22 body
23 thumb
24 other finger
25 other finger
26 finger stall
27 closed end of finger stall
28
29
30 third embodiment
31 cuff
32 body
33 finger stall
34 finger stall
35 closed end of finger stall
36 closed end of finger stall
37 side opening
38
39
40 extra elastic
41 grasped object
42 spoon
43
44
45

I claim:

1. A method of deterring a child's habit of finger sucking to be performed by and under the complete control of the child comprising all of the enumerated the steps of:
    obtaining at least two finger sucking deterrent devices made of a knitted fabric, each comprising:
        a resilient cuff configured to be placed on the wrist and easily removed therefrom and also to be moved upward on the arm and retained thereon;
        at least one stretchable tubular finger stall with a closed upper end and a lower end, said at least one finger stall being sized to accommodate at least one finger and adapted to enable the child to remove the at least one finger from the at least one finger stall while retaining the device on the hand and to move the device upward on the arm and thereafter move the device downward on the arm and replace the at least one finger in the at least one finger stall, said at least one finger stall being composed of a fabric that permits air to pass through it; and
        a stretchable body for joining the at least one finger stall to the cuff, said body having at least one opening of sufficient size for the device to be put on and taken off with ease and so that the child can remove the at least one finger from the at least one finger stall and replace the at least on finger into the at least one finger stall while retaining the device on the hand;
    covering the at least one finger to be sucked with the finger stall of the one of the at least two finger sucking deterrent devices being worn on the hand;
    removing the at least one finger from the at least one finger stall and pushing the device upward on his or her arm during eating and washing;
    moving the device downward on the arm and replacing the at least one finger into the at least one finger stall after eating and washing;
    sucking on the at least one finger through the at least one finger stall and having air pulled through the fabric so that he or she gets a dry and unpleasant mouth feel and obtains no satisfaction in the sucking;
    removing the at least one finger from the at least one finger stall and moving the device upward on the arm during a school activity;
    moving the device downward on the arm and replacing the at least one finger into the at least one finger stall after completion of the school activity;
    replacing the device with another of the at least two devices when the one device becomes soiled;
    removing the device from his or her hand when bathing and replacing the device on his or her hand thereafter; and
    wearing one of the at least two devices twenty four hours a day until he or she no longer sucks his or her at least one finger except when putting on a clean deterrent device or when bathing;
    whereby, as the child repeatedly sucks his or her at least one finger through the at least one finger stall no suction is attained, there is an unappealing mouth feel and gradually the child loses interest in sucking the at least one finger and can cease wearing the device altogether.

2. A method of deterring a child's habit of finger sucking to be performed by and under the sole and complete control of the child and utilizing an article of manufacture in the form of a finger sucking deterrent device of a type made of a knitted fabric and having a resilient cuff configured to be placed on the wrist, moved upward on the arm, retained thereon, moved back to the wrist and removed from the wrist; a stretchable tubular finger stall with a closed upper end and a lower end, sized to accommodate at least one finger and adapted to enable the child to remove the at least one finger from the finger stall and replace the at least one finger into the finger stall while retaining the device on the hand, the finger stall being composed of a fabric that permits air to pass through it; and a stretchable body for joining the finger stall to the cuff and configured to enable the child to remove the at least one finger from the finger stall and replace the at least one finger into the finger stall, push the device upward on the arm and move the device back to the wrist while retaining the device on the hand and to put on and take off the device; said method comprising all of the enumerated steps of:
    (a) obtaining at least two finger sucking deterrent devices;
    (b) covering the at least one finger to be sucked with the finger stall of the one of the at least two finger sucking deterrent devices being worn on the hand;
    (c) removing the at least one finger from the finger stall without removing the device from the hand and pushing the device upward on his or her arm during eating, hygienic activities and washing;
    (d) moving the device downward on the arm and replacing the at least one finger into the finger stall without removing the device from the hand after eating, hygienic activities and washing;
    (e) sucking on the at least one finger through the finger stall and having air pulled through the fabric so that no suction is attained and he or she gets no satisfaction in the sucking;
    (f) removing the at least one finger from the finger stall without removing the device from the hand and moving the device upward on the arm during a school activity;
    (g) moving the device downward on the arm and replacing the at least one finger into the finger stall without removing the device from the hand after completion of the school activity;
    (h) replacing the device with another of the at least two devices when the one device becomes soiled;
    (i) removing the device from his or her hand when bathing and replacing the device on his or her hand thereafter; and (j) wearing one of the at least two devices twenty four hours a day until he or she no longer sucks his or her at least one finger except when putting on a clean deterrent device or when bathing;

whereby, as the child repeatedly sucks his or her at least one finger through the finger stall no suction is attained, there is an unappealing mouth feel and gradually the child loses interest in and ceases sucking the at least one finger and can stop wearing the device altogether.

* * * * *